United States Patent
Travish et al.

(10) Patent No.: US 10,524,743 B2
(45) Date of Patent: Jan. 7, 2020

(54) METHOD OF DESIGNING AN X-RAY EMITTER PANEL

(71) Applicant: ADAPTIX LTD, Oxfordshire (GB)

(72) Inventors: Gil Travish, Oxfordshire (GB); Raphael Hauser, Oxfordshire (GB)

(73) Assignee: Adaptix Ltd., Oxfordshire (GB)

(*) Notice: Subject to any disclaimer, the term of this patent is extended or adjusted under 35 U.S.C. 154(b) by 297 days.

(21) Appl. No.: 15/516,335

(22) PCT Filed: Oct. 12, 2015

(86) PCT No.: PCT/IB2015/057792
§ 371 (c)(1),
(2) Date: Mar. 31, 2017

(87) PCT Pub. No.: WO2016/059535
PCT Pub. Date: Apr. 21, 2016

(65) Prior Publication Data
US 2017/0245814 A1 Aug. 31, 2017

(30) Foreign Application Priority Data
Oct. 16, 2014 (GB) .................................. 1418391.7

(51) Int. Cl.
*A61B 6/00* (2006.01)
*H01J 35/06* (2006.01)
*A61B 6/02* (2006.01)
*H01J 1/304* (2006.01)

(52) U.S. Cl.
CPC ............ *A61B 6/4007* (2013.01); *H01J 35/06* (2013.01); *H01J 35/064* (2019.05); *H01J 35/065* (2013.01); *A61B 6/025* (2013.01); *H01J 1/3048* (2013.01); *H01J 2201/30469* (2013.01); *H01J 2235/068* (2013.01)

(58) Field of Classification Search
CPC ...... A61B 6/4007; H01J 35/06; H01J 35/065; H01J 35/064
USPC ..................... 378/92, 122, 124, 91
See application file for complete search history.

(56) References Cited

U.S. PATENT DOCUMENTS

| | | | |
|---|---|---|---|
| 6,181,764 B1 | 1/2001 | Solomon | |
| 6,233,309 B1* | 5/2001 | Baptist | G03B 42/047 378/162 |
| 6,259,765 B1* | 7/2001 | Baptist | H01J 35/065 313/309 |
| 6,333,968 B1* | 12/2001 | Whitlock | B82Y 10/00 378/122 |
| 6,456,691 B2* | 9/2002 | Takahashi | B82Y 10/00 378/122 |
| 6,553,096 B1* | 4/2003 | Zhou | A61B 6/4028 378/122 |
| 6,556,656 B2* | 4/2003 | Hess | H01J 35/06 378/136 |

(Continued)

FOREIGN PATENT DOCUMENTS

WO 2016059535 4/2016

*Primary Examiner* — Allen C. Ho
(74) *Attorney, Agent, or Firm* — Blueshift IP, LLC; Robert Plotkin

(57) ABSTRACT

A method of designing an x-ray emitter panel 100 including the step of determining a pitch scale, r, to be used in placing x-ray emitter elements 110 on the panel 100, thereby arriving at a specific design of x-ray emitter panel 100 suitable for a specific use.

13 Claims, 3 Drawing Sheets

(56) References Cited

U.S. PATENT DOCUMENTS

| | | | | |
|---|---|---|---|---|
| 6,674,837 B1* | 1/2004 | Taskar | | A61B 6/00 378/122 |
| 6,760,407 B2* | 7/2004 | Price | | H01J 35/065 378/119 |
| 6,975,703 B2* | 12/2005 | Wilson | | H01J 35/30 378/124 |
| 7,023,950 B1* | 4/2006 | Annis | | G01N 23/046 378/119 |
| 7,082,182 B2* | 7/2006 | Zhou | | A61B 6/032 378/10 |
| 7,103,138 B2* | 9/2006 | Pelc | | A61B 6/032 378/4 |
| 7,145,981 B2* | 12/2006 | Pelc | | A61B 6/032 378/9 |
| 7,192,031 B2* | 3/2007 | Dunham | | A61B 6/032 378/122 |
| 7,295,651 B2* | 11/2007 | Delgado | | G01N 23/046 378/10 |
| 7,399,987 B1* | 7/2008 | Viscor | | B82Y 10/00 257/10 |
| 7,873,146 B2* | 1/2011 | Okunuki | | H01J 35/065 378/122 |
| 7,940,888 B2* | 5/2011 | Tsujii | | A61B 6/4007 378/21 |
| 7,945,015 B2* | 5/2011 | Tsujii | | A61B 6/00 378/124 |
| 7,976,218 B2* | 7/2011 | Vermilyea | | G21K 1/025 378/124 |
| 7,991,114 B2* | 8/2011 | Okunuki | | A61B 6/032 378/11 |
| 7,991,120 B2* | 8/2011 | Okunuki | | A61B 6/00 378/122 |
| 8,229,074 B2* | 7/2012 | Mahapatra | | H01J 35/065 378/122 |
| 8,306,184 B2* | 11/2012 | Chang | | A61N 5/103 378/62 |
| 8,447,011 B2* | 5/2013 | Ohta | | A61B 6/00 378/62 |
| 8,488,742 B2* | 7/2013 | Tsujii | | A61B 6/4441 378/138 |
| 8,699,657 B2* | 4/2014 | Baeumer | | A61B 6/032 250/494.1 |
| 8,774,351 B2* | 7/2014 | Funk | | A61B 6/4488 378/62 |
| 9,053,890 B2* | 6/2015 | Sun | | H01J 9/025 |
| 9,217,719 B2* | 12/2015 | Lowell | | H01J 35/04 |
| 9,281,157 B2* | 3/2016 | Utsumi | | A61B 6/40 |
| 9,398,677 B2* | 7/2016 | Tang | | H05G 1/32 |
| 9,478,385 B2* | 10/2016 | Kim | | H01J 35/06 |
| 9,490,099 B2* | 11/2016 | Mackie | | A61B 6/035 |
| 9,506,877 B2* | 11/2016 | Koh | | G01N 23/046 |
| 9,517,043 B2* | 12/2016 | Tamura | | A61B 6/025 |
| 9,603,575 B2* | 3/2017 | Koh | | A61B 6/4452 |
| 9,653,247 B2* | 5/2017 | Tang | | H01J 35/02 |
| 9,653,251 B2* | 5/2017 | Tang | | H01J 35/14 |
| 9,719,947 B2* | 8/2017 | Yun | | G01N 23/20075 |
| 9,734,979 B2* | 8/2017 | Tang | | H01J 35/24 |
| 9,748,069 B2* | 8/2017 | Kim | | A61B 6/02 |
| 9,761,404 B2* | 9/2017 | Tang | | H01J 35/06 |
| 9,782,136 B2* | 10/2017 | Zhou | | A61B 6/547 |
| 9,833,205 B2* | 12/2017 | Sugie | | A61B 6/06 |
| 9,897,557 B2* | 2/2018 | Kim | | G01N 23/046 |
| 9,922,793 B2* | 3/2018 | Hori | | H01J 29/46 |
| 10,014,148 B2* | 7/2018 | Tang | | H01J 35/065 |
| 10,165,993 B2* | 1/2019 | Kim | | A61B 6/4007 |
| 10,217,598 B2* | 2/2019 | Evans | | H01J 35/065 |
| 10,242,836 B2* | 3/2019 | Iida | | H01J 35/065 |
| 10,269,527 B2* | 4/2019 | Kenmotsu | | H01J 1/3042 |
| 2009/0232270 A1 | 9/2009 | Okunuki | | |
| 2009/0232272 A1 | 9/2009 | Tsujii | | |
| 2010/0098218 A1 | 4/2010 | Vermilyea | | |
| 2010/0266097 A1 | 10/2010 | Okunuki | | |
| 2010/0329416 A1 | 12/2010 | Tsujii | | |
| 2011/0038465 A1 | 2/2011 | Mahapatra | | |
| 2011/0280367 A1 | 11/2011 | Baeumer | | |
| 2012/0051510 A1 | 3/2012 | Ohta | | |
| 2014/0192955 A1 | 7/2014 | Lowell | | |

* cited by examiner

METHOD OF DESIGNING AN X-RAY EMITTER PANEL

The present invention relates generally to a method of designing an x-ray emitter panel.

Medical imaging with X-rays has been common for the past century. Planar radiology is the most common medical imaging modality. At the heart of the approach lies an x-ray source, comprising vacuum-tubes capable of generating a single cone or fan beam of x-rays over a wide range of energies and currents. However, the imaging geometries possible with these substantially point-like sources is limited; that is, the source must be placed a significant distance away from the object to be imaged in order that the cone or fan covers sufficient area. A minimum value of this distance (usually called the Source to Object Distance, SOD, or stand-off distance) can be determined trivially by trigonometric means using values of the opening angle of the x-ray of the cone and a desired coverage width of the object to be imaged.

In practice, the minimum distance to a point-like source is usually set by the so-called "skin safe distance". Essentially, the peak dose from a fan or cone source is at the entrance to the body (typically the skin) and hence the minimum distance is restricted to that which would cause an excessive dose at the entry point.

When a single, substantially point-like source of x-rays is used, magnification is governed by the ratio of the Source to Object Distance (SOD) to the Source to Image Distance (SID).

In order to take multiple images of an object from a variety of directions, a mechanical gantry is typically used to move a single source along a sequence of locations. An alternative has been proposed in which multiple sources are placed at fixed locations around an object, each source being selectively activated. Such a system, would allow for a shorter overall period of image capture; however, this system is prohibitive due to the cost of the sources, and their relative bulk would afford only a limited number of viewing angles.

A common alternative approach to producing multiple x-ray sources is to produce multiple cathodes (or emitters) in a 'source array' or 'emitter array'. In particular, Field Enhanced Emitter (FEE) arrays, sometimes referred to as Field Emitter Arrays (FEAs), such as Spindt arrays, may be used in x-ray tubes and serve as an advanced cathode. For instance, an array of moderate field enhancement tips may operate at high voltages as emitters for x-ray production. Cathodes produced from carbon nanotubes (CNTs) may offer extreme field enhancement and hence may allow for control of electron emission at low voltages. In all cases, such FEAs allow for multiple sources of x-rays from an extended or distributed source. In the case of flat-panel sources, the size of the arrays can be large and allow for significant displacement from a source on one corner of the array to a source on the opposite corner.

These approaches allow for tomosynthesis, but impose more complex geometric constraints. For instance, each emitter in the array produces its own x-ray cone (referred to herein as a 'conelet'). In order for complete coverage of an object, there must be a certain amount of overlap of the conelets; however, the image formed by the object will include multiple images or shadows (such as double images) due to illumination of features from multiple angles.

Prior methods of addressing these issues have included the use of so-called anti-scatter grids, which also find use in the formation of conventional x-rays images. However, while these devices serve to limit the acceptance angle of x-rays to the detector, they also limit the information available for a given dose. Therefore, it is desirable to preserve all the available information, and separate the overlaps in software (and/or use a variable number of conelets to obtain more information about an object). With sufficient prior knowledge of aspects of an object, it is possible to separate spatiotemporally overlapping conelets; however, detailed knowledge of the aspects of an object are not always available. Hardware methods such as structured light can further assist in the software image reconstruction; however, in general, and in medical imaging where prior knowledge is often limited in particular, it is usually desirable to have temporally separated images, and then use other reconstruction methods to render a 3D model of the object.

A wide range of methods have been considered in the literature for image reconstruction. With both deterministic emitter and detector locations, it is possible to apply powerful methods to determine 3D information about the object with only the most rudimentary assumptions. The various methods are often referred to as compressed sensing, basis pursuit and sparse inverse problems. Regardless of the specific approach, voxelization of the space to be imaged is typically used to define the smallest image volume. Iterative methods may then be employed to determine the set of voxel values which best fit the object (and reduce a value function to a minimum). The voxelization of the image volume as well as the information that can be recovered are largely determined by the emitter geometry and the SOD and SID.

According to a first aspect of the present invention, there is provided a method of designing an x-ray emitter panel for use as a distributed x-ray source, the x-ray emitter panel for use with an x-ray detector panel, the method comprising the steps of choosing a predetermined total number of photons produced by a charge available for a single exposure, $E_{tot}$; and choosing a predetermined surface area of the emitter panel, F;

choosing a predetermined absorption factor due to tissue placed between the emitter panel and the detector panel, $\eta_{bre}$;

choosing a predetermined maximum emitter-detector panel separation, $D_{max}$;

choosing a predetermined minimum number of photons that is required to arrive at a detector in the detector panel in order to obtain a viable image, $E_{min}$;

choosing a predetermined density of detectors in the detector panel, $\rho_{det}$;

choosing a predetermined dimensionless constant having a value between approximately 10 and 20, A;

solving an inequality of the form:

$$\frac{\left(\frac{r}{D_{max}}\right)^2}{\left(1+\left(\frac{r}{D_{max}}\right)^2\right)^{\frac{3}{2}}} \geq \frac{A\rho_{det}FE_{min}}{E_{tot}\eta_{bre}}$$

for r;

selecting a pitch scale corresponding to a value of r determined from the solution of the inequality.

The step of choosing may comprise selecting a desired value and/or determining an actual value possessed by components intended to be used in manufacture of the designed x-ray emitter panel, for instance by testing.

The method may further comprise selecting an array pattern for placement of x-ray emitters. The array pattern may comprise a grid of triangles, for instance equilateral triangles. Alternatively or additionally, the array pattern may be a grid of squares, rectangles and/or hexagons. The array pattern may be a substantially pseudorandom array pattern.

The array pattern may be a combination of array patterns. For instance, the array pattern may be a combination of two, three, four or five overlapping array patterns. The array patterns may have respective pitch scales that differ between array patterns.

A may be between approximately 1 and 20, in particular between approximately 1 and 16. The choice of value of A may depend on the geometry of the system, and in particular the type of array. In particular, A may be related to the emitter density on the panel. The emitter density of a panel may be proportional to the inverse of the square of the pitch scale r, and A may be proportional to the same constant of proportionality. That is, if the emitter density of a panel may be calculated as:

$$\frac{B}{r^2}$$

then:

$$A \propto B$$

In particular, for a triangular array B may be approximately equal to $8\sqrt{3}$, and for a square array B may be approximately equal to 1.

More particularly, A may be defined as follows:

$$A \approx 2\pi B\left(1 - \cos\frac{7\pi}{36}\right)$$

For a triangular array, A may be between approximately 12 and 21, in particular between approximately 13 and 18, more particularly between approximately 14 and 17. A may be between approximately 15 and 16, in particular A may be between approximately 15.5 and 16, more particularly A may be approximately 15.7. A may be approximately 15.72.

For a square array, A may be between approximately 0.5 and 3, in particular between approximately 0.8 and 2, more particularly between approximately 1 and 1.5. A may be between approximately 1.1 and 1.3, in particular A may be between approximately 1.1 and 1.2, more particularly A may be approximately 1.14. A may be approximately 1.136.

Other array patterns are envisaged with corresponding values of A and/or B as would be understood by the skilled person.

$\rho_{det}$ may be a predetermined average (e.g. mean) density of detectors in the detector panel. $\rho_{det}$ may have a value between approximately $10^3$ m$^{-2}$ and $10^{10}$ m$^{-2}$, in particular between approximately $10^7$ m$^{-2}$ and $5 \times 10^9$ m$^{-2}$, more particularly between approximately $5 \times 10^7$ m$^{-2}$ and $2 \times 10^9$ m$^{-2}$, for instance, approximately $5.1 \times 10^7$ m$^{-2}$, $10^8$ m$^{-2}$, or $1.1 \times 10^9$ m$^{-2}$.

F may be between approximately 0.05 m$^2$ and 0.3 m$^2$, in particular between approximately 0.1 m$^2$ and 0.2 m$^2$, more particularly between approximately 0.12 m$^2$ and 0.18 m$^2$, for instance approximately 0.12 m$^2$, 0.16 m$^2$, 0.17 m$^2$ or 0.18 m$^2$. For instance, the emitter panel may have dimensions of 0.3 m, 0.4 m, and/or 0.42 m.

$E_{min}$ may be between approximately 10 and 1500, in particular between approximately 500 and 1200, more particularly between approximately 800 and 1100, for instance approximately 1000.

$E_{tot}$ may be between approximately $1 \times 10^{12}$ and $1 \times 10^{17}$ or may be between approximately $1 \times 10^{13}$ and $1 \times 10^{16}$, in particular between approximately $1 \times 10^{14}$ and $1 \times 10^{15}$, more particularly between approximately $2 \times 10^{14}$ and $8 \times 10^{14}$, for instance approximately $6 \times 10^{14}$.

$\eta_{bre}$ may be between approximately 0.001 and 0.1, in particular between approximately 0.005 and 0.05, more particularly between approximately 0.008 and 0.03, for instance approximately 0.01.

The pitch scale may be referred to as the emitter scale and may be between approximately 0.01 m and 0.1 m, in particular between approximately 0.02 m and 0.09 m, more particularly between approximately 0.03 m and 0.08 m, for instance approximately 0.0100 m, 0.0182 m, 0.0212 m, 0.0363 m or 0.0872 m.

The emitter pitch may be statistically defined as the average distance between adjacent emitters; that is, the distance between successive emitters in the array. In a regular array, the distance between successive emitters in the array is invariant; however, in a pseudorandom arrangement, the average may be taken. In some arrays, the emitter pitch and/or the pitch scale may vary across the array, particularly at the edges. The emitter pitch may be between approximately 1 and 4 times the value of r; in particular between approximately 1 and 3.5 times, more particularly between approximately 1.5 and 3 times; for instance, between approximately 2 and 2.5 times. The emitter pitch may be defined as r (for a square grid), $$\left(\frac{r}{\sqrt{12}}\right)$$

(for a triangular grid), 1.5r, 2r, 2.5r, 3r or 3.5r, and may be between approximately 0.0001 m or 0.001 m and 0.05 m, in particular between approximately 0.005 and 0.02 m, more particularly approximately 0.01 m.

Solving the inequality may comprise finding an approximate solution.

Solving the inequality may comprise selecting a minimum value of the pitch scale r which satisfies the inequality.

Solving the inequality may comprise solving the equation:

$$\frac{\left(\frac{r}{D_{max}}\right)^2}{\left(1+\left(\frac{r}{D_{max}}\right)^2\right)^{\frac{3}{2}}} = \frac{A\rho_{det}FE_{min}}{E_{tot}\eta_{bre}}$$

Solving the equation may comprise applying Newton's method.

The method may further comprise the step of selecting a collimation angle, $\alpha$, that is less than or equal to (or simply less than) twice the arctangent of the ratio of the selected pitch scale r to the maximum emitter-detector panel separation $D_{max}$; for example:

$$\alpha \leq 2\tan^{-1}\frac{r}{D_{max}}$$

The method may further comprise the step of selecting a collimation angle, α, that is substantially equal to twice the arctangent of the ratio of the selected pitch scale r to the maximum emitter-detector panel separation $D_{max}$; that is:

$$\alpha = 2\tan^{-1}\frac{r}{D_{max}}$$

α may be between approximately 5° and 70°, in particular between approximately 10° and 40°, more particularly between approximately 15° and 30°, for instance approximately 20°, 20.6°, 23° and/or 24°.

The method may further comprise the step of selecting a collimation angle, α, that satisfies the inequality:

$$\alpha \geq 2\tan^{-1}\frac{rM_{design}}{4\delta_{design}}$$

in which:

$\delta_{design}$ is a predetermined desired stand-off distance of the emitter panel from the tissue placed between the emitter panel and the detector panel; and $M_{design}$ is a predetermined factor representative of a multiplicity of overlapping conelets from adjacent x-ray emitters on a given part of the tissue.

$M_{design}$ may be determined by solving the further equation:

$$M_{design} = 4 - \frac{d_{design}}{D_{design}}$$

in which:

$d_{design}$ is a predetermined desired thickness of tissue placed between the emitter panel and the detector panel; and $D_{design}$ is a predetermined desired emitter-detector panel separation, less than $D_{max}$.

As can be appreciated by referring to FIG. 1, the tissue thickness d, stand-off distance from the emitter panel to the tissue δ, and the separation between the emitter panel and the detector D are related by:

$$D = d + \delta$$

The above relations can similarly be applied to maximal, actual and design variables as well, as would be understood by the skilled person. For instance, in actual use (during x-ray imaging), the variables may differ from the design variables. Thus, the method may further comprise a relation between the collimation angle, α, and the other variables in use satisfies the inequality:

$$\alpha \geq 2\tan^{-1}\frac{rM_{actual}}{4\delta_{actual}}$$

in which:

$\delta_{actual}$ is the actual stand-off distance of the emitter panel from the tissue placed between the emitter panel and the detector panel; and $M_{actual}$ is a factor representative of a multiplicity of overlapping conelets from adjacent x-ray emitters on a given part of the tissue.

$M_{actual}$ may be determined by solving the further equation:

$$M_{actual} = 4 - \frac{d_{actual}}{D_{actual}}$$

in which:

$d_{actual}$ is the actual thickness of tissue placed between the emitter panel and the detector panel; and $D_{actual}$ is the actual emitter-detector panel separation, less than $D_{max}$.

A lower limit for α may be given by $$2\tan^{-1}\frac{r}{\delta}\left(1 - \frac{d}{D}\right).$$

It will be appreciated that the above relations are not all independent.

$D_{max}$ may be determined based on an imaging modality. The method may further comprise determining $D_{max}$.

$D_{max}$ may be determined by solving the further equation:

$$D_{max} = \frac{4d_{max}}{4 - M_{min}}$$

in which:

$d_{max}$ is a predetermined maximum thickness of tissue placed between the emitter panel and the detector panel; and $M_{min}$ is a predetermined minimum value of a factor representative of a multiplicity of overlapping conelets from adjacent x-ray emitters on a given part of the tissue, wherein $M_{min}$ has a value between 1 and 4.

$D_{max}$ may be between approximately 0.05 m and 2 m, in particular between approximately 0.07 m and 1 m, more particularly between approximately 0.08 m and 0.5 m, for instance 0.1 m, 0.2 m, 0.4 m, 0.48 m and/or 0.5 m. It may be between approximately 0.2 m and 0.4 m.

$d_{max}$ may be between approximately 0.01 m and 1 m, in particular 0.05 m and 0.4 m, more particularly between approximately 0.1 m and 0.3 m, for instance 0.05 m or 0.3 m.

$M_{min}$ may be determined based on a consideration of the specific image reconstruction approach used and the desired speed of imaging, where here the speed may include the complete process of image acquisition and processing. The method may further comprise determining $M_{min}$.

$M_{min}$ may be determined based on a minimum value of $M_{actual}$.

In general, a larger $M_{min}$ corresponds to more information available for image reconstruction and a longer period being required to obtain the image. $M_{min}$ may be between approximately 1 and 3.9, in particular between approximately 1 and 3.7, more particularly between approximately 1 and 3.6, for instance approximately 1.5, 2, 3 or 3.6.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
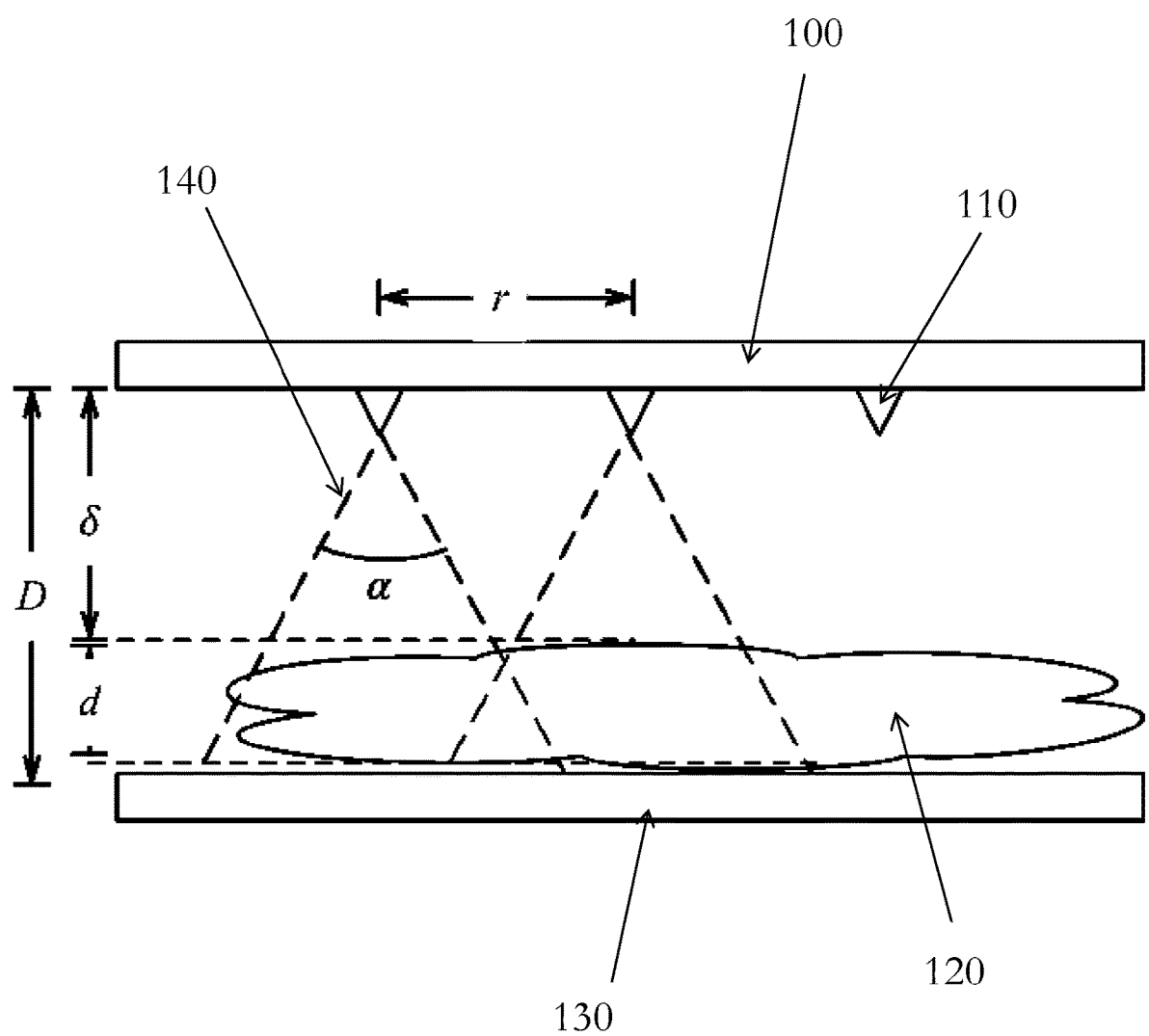
FIG. 1 is a schematic cross-sectional representation of an emitter array in use.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances.

The principles of the invention will now be described by a detailed description of at least one drawing relating to exemplary features of the invention. It is clear that other arrangements can be configured according to the knowledge of persons skilled in the art without departing from the underlying concept or technical teaching of the invention, the invention being limited only by the terms of the appended claims.

FIG. 1 shows an emitter array 100 including a plurality of emitter elements 110. Each emitter element 110 is configured to emit x-rays 140 over a collimation angle $\alpha$. The emitter array 100 is shown in use such that x-rays 140 from the emitter elements 110 may pass through a body 120 having an approximate thickness d, spaced a distance $\delta$ from the emitter array 100, to be detected by a detector panel 130 that is spaced a distance D from the emitter array 100.

Figure 2:
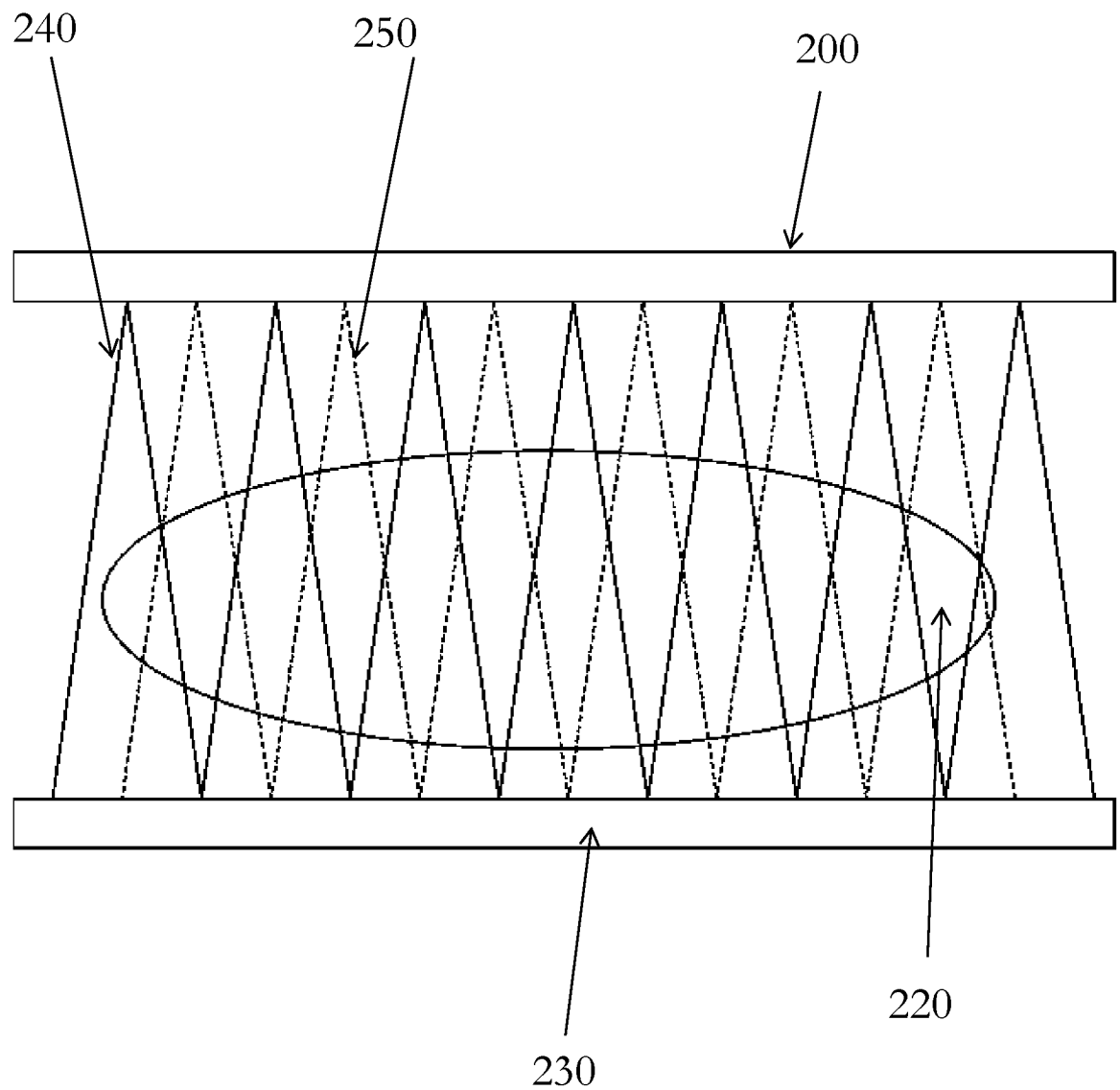
FIG. 2 is a schematic cross-sectional representation of an emitter array in use.

FIG. 2 shows an emitter array 200 including a first plurality of emitter elements and a second plurality of emitter elements (not shown). X-rays 240 (shown in solid lines) from an emitter element in the first plurality of emitter elements are arranged such that they do not overlap with x-rays from adjacent emitter elements in the first plurality of emitter elements before arriving at a detector panel 230

(after passing through tissue to be examined 220). This prevents multiple images being formed of a single feature in the tissue 220. Similarly, x-rays 250 (shown in dotted lines) from an emitter element in the second plurality of emitter elements are arranged such that they do not overlap with x-rays from adjacent emitter elements in the second plurality of emitter elements before arriving at a detector panel 230 (after passing through tissue to be examined 220). By using each plurality of emitter elements separately (i.e. spaced in time, temporal separation), a greater coverage of the tissue 220 may be made. In the arrangement shown in FIG. 2, at least one further plurality of emitter elements may also be used to build complete coverage of the tissue 220 in a similar way.

Figure 3:
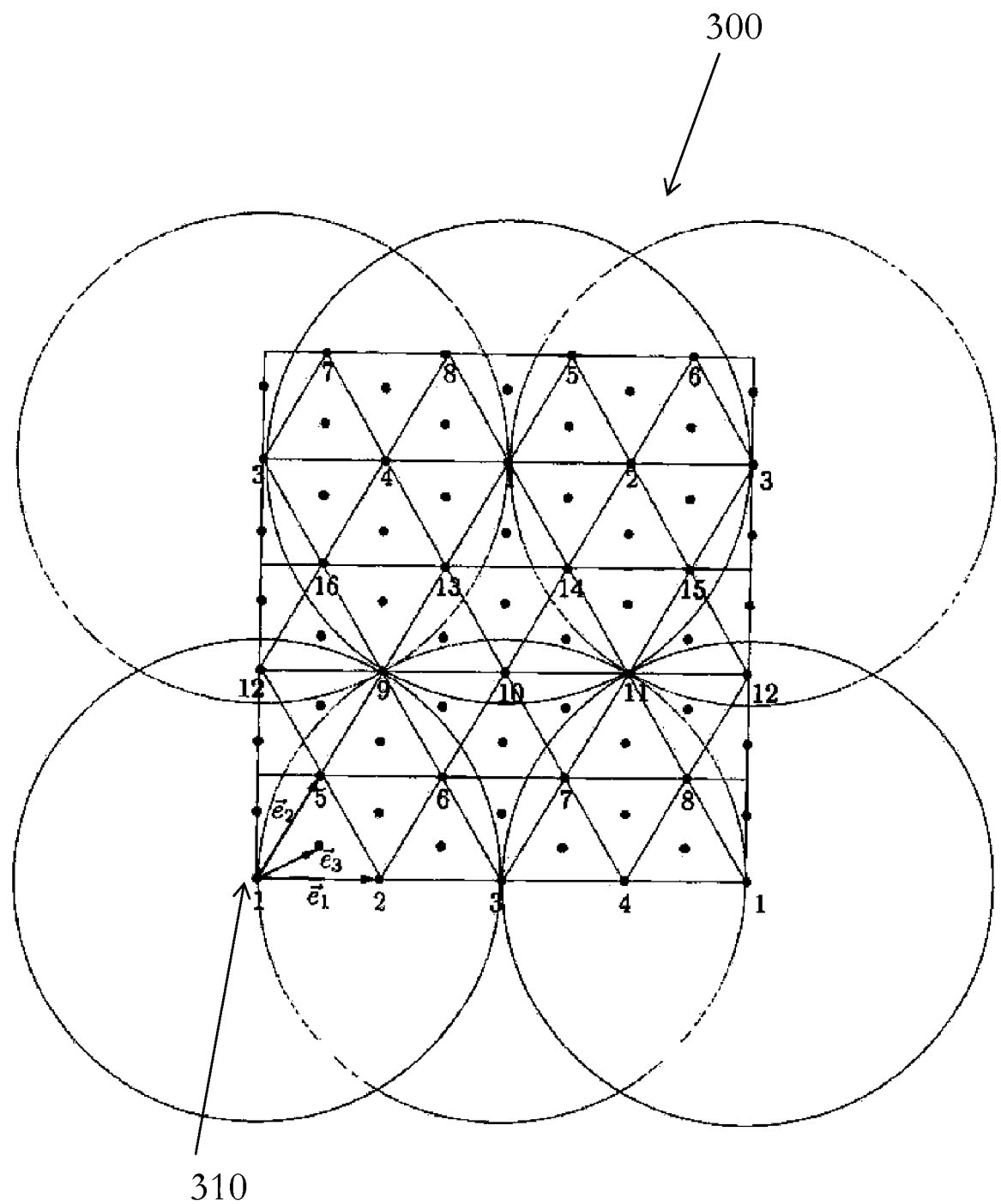
FIG. 3 is a schematic plan-view representation of an emitter array.

FIG. 3 is a schematic plan-view representation of an emitter array 300. Each emitter element 310 is arranged with its centre at node points of a grid of equilateral triangles. That is, the centres are located at points:

$$2r(k\vec{e_1} + l\vec{e_2}), k, l \in \mathbb{Z}$$

where:

$$\vec{e_1} = \begin{pmatrix} 1 \\ 0 \end{pmatrix}$$

$$\vec{e_2} = \begin{pmatrix} \cos\frac{\pi}{3} \\ \sin\frac{\pi}{3} \end{pmatrix}$$

and $\mathbb{Z}$ denotes the set of integers such that the defined points fit on a given panel. This pattern is shifted such that the panel is covered homogenously by 48 exposures enumerated by the formula $$f+4(g-1)+16(h-1), (f=1, \ldots, 4; g=1, \ldots, 4; h=1, \ldots, 3)$$

The centres of circles that are fired simultaneously in exposure (f, g, h) are given by:

$$r\left(\frac{f-1}{2}\vec{e_1} + \frac{g-1}{2}\vec{e_2} + \frac{h-1}{2\sqrt{3}}\vec{e_3} + 2k\vec{e_1} + 2l\vec{e_2}\right)$$

where:

$$\vec{e_3} = \begin{pmatrix} \cos\frac{\pi}{6} \\ \sin\frac{\pi}{6} \end{pmatrix}$$

The first 16 exposures (corresponding to h=1) are obtained by shifting the parent pattern to the nodes obtained by bisecting the grid of equilateral triangles twice.

The second and third group of 16 exposures are centred where the first set of exposures left holes (regions not covered by radiation). There are twice as many holes as disks in any given exposure, which leads to the three sets of 16.

Note that all emitters except those near the boundary of the panel are equidistant to their six nearest neighbours, the distance being $$\left(\frac{r}{\sqrt{12}}\right).$$

We call this distance emitter pitch, while we refer to r as the emitter scale. The emitter scale also has the interpretation as radius of the non-overlapping disks of radiation that reach the detector panel simultaneously in any given exposure. r may be chosen such that these disks are just touching.

The invention claimed is:

1. A method of manufacturing an x-ray emitter panel including an array of x-ray emitters for use as a distributed x-ray source, the x-ray emitter panel for use with an x-ray detector panel, the method comprising the steps of:
    choosing a predetermined total number of photons produced by a charge available for a single exposure, $E_{tot}$; and
    choosing a predetermined surface area of the x-ray emitter panel, F;
    choosing a predetermined absorption factor due to tissue placed between the x-ray emitter panel and the x-ray detector panel, $\eta_{bre}$;
    choosing a predetermined maximum emitter-detector panel separation, $D_{max}$;
    choosing a predetermined minimum number of photons that is required to arrive at a detector in the x-ray detector panel in order to obtain a viable image, $E_{min}$;
    choosing a predetermined density of detectors in the x-ray detector panel, $\rho_{det}$;
    choosing a predetermined dimensionless constant having a value between 10 and 20, A;
    solving an inequality of the form:

$$\frac{\left(\frac{r}{D_{max}}\right)^2}{\left(1 + \left(\frac{r}{D_{max}}\right)^2\right)^{\frac{3}{2}}} \geq \frac{A\rho_{det}FE_{min}}{E_{tot}\eta_{bre}}$$

for r;
    selecting a pitch scale corresponding to a value of r determined from a solution of the inequality; and
    constructing an x-ray emitter panel having a surface area equal to F, the x-ray emitter panel comprising an array of x-ray emitters arranged in the x-ray emitter panel with the pitch scale corresponding to the value of r determined from the solution of the inequality, the x-ray emitter panel configured to produce a total number of photons during a single exposure equal to $E_{tot}$.

2. The method of claim 1, wherein solving the inequality comprises finding an approximate solution.

3. The method of claim 1, wherein solving the inequality comprises selecting a minimum value of the pitch scale r which satisfies the inequality.

4. The method of claim 1, wherein solving the inequality comprises solving an equation:

$$\frac{\left(\frac{r}{D_{max}}\right)^2}{\left(1 + \left(\frac{r}{D_{max}}\right)^2\right)^{\frac{3}{2}}} = \frac{A\rho_{det}FE_{min}}{E_{tot}\eta_{bre}}.$$

5. The method of claim 4, wherein solving the equation comprises applying Newton's method.

6. The method of claim 1, further comprising the step of selecting a collimation angle, α, that is less than or equal to twice an arctangent of a ratio of the selected pitch scale r to the predetermined maximum emitter-detector panel separation $D_{max}$; that is:

$$\alpha \le 2\tan^{-1}\frac{r}{D_{max}}.$$

7. The method of claim 6, further comprising the step of selecting a collimation angle α, that is substantially equal to twice the arctangent of the ratio of the selected pitch scale r to the predetermined maximum emitter-detector panel separation $D_{max}$; that is:

$$\alpha = 2\tan^{-1}\frac{r}{D_{max}}.$$

8. The method of claim 1, further comprising the steps of:
choosing a predetermined desired stand-off distance of the x-ray emitter panel from the tissue placed between the x-ray emitter panel and the x-ray detector panel, $\delta_{design}$;
choosing a predetermined factor representative of a multiplicity of overlapping conelets from adjacent x-ray emitters on a given part of the tissue, $M_{design}$; and
solving a second inequality of the form:

$$\alpha \ge 2\tan^{-1}\frac{rM_{design}}{4\delta_{design}}$$

selecting a collimation angle corresponding to a value of α, determined from a solution of the second inequality.

9. The method of claim 8, further comprising the steps of:
choosing a predetermined desired thickness of the tissue placed between the x-ray emitter panel and the x-ray detector panel, $d_{design}$;
choosing a predetermined desired emitter-detector panel separation, $D_{design}$, less than $D_{max}$; and determining $M_{design}$ by solving a further equation:

$$M_{design} = 4 - \frac{d_{design}}{D_{design}}.$$

10. The method of claim 8, wherein the step of choosing the predetermined minimum value of a factor, $M_{min}$, comprises determining $M_{min}$ based on a consideration of a specific image reconstruction approach used, a desired speed of imaging, and a minimum value of $M_{design}$.

11. The method of claim 1, wherein the step of choosing the predetermined maximum emitter-detector panel separation, $D_{max}$, comprises choosing the predetermined maximum emitter-detector panel separation, $D_{max}$, based on an imaging modality.

12. The method of claim 1, further comprising the steps of:
choosing a predetermined maximum thickness of the tissue placed between the x-ray emitter panel and the x-ray detector panel, $d_{max}$; and
choosing a predetermined minimum value of a factor, $M_{min}$ representative of a multiplicity of overlapping conelets from adjacent x-ray emitters on a given part of the tissue, wherein $M_{min}$ has a value between 1 and 4;
determining $D_{max}$ by solving a further equation:

$$D_{max} = \frac{4d_{max}}{4 - M_{min}}.$$

13. The method of claim 12, wherein the step of choosing the predetermined minimum value of the factor, $M_{min}$, comprises determining $M_{min}$ based on a consideration of a specific image reconstruction approach used and a desired speed of imaging.

* * * * *